United States Patent
Suzuki et al.

(10) Patent No.: US 10,625,200 B2
(45) Date of Patent: Apr. 21, 2020

(54) CARBON DIOXIDE ABSORBENT AND APPARATUS OF SEPARATING AND RECOVERING CARBON DIOXIDE

(71) Applicant: Kabushiki Kaisha Toshiba, Minato-ku (JP)

(72) Inventors: Akiko Suzuki, Ota (JP); Asato Kondo, Yokohama (JP); Takashi Kuboki, Ota (JP); Shinji Murai, Sagamihara (JP); Mitsuru Udatsu, Kawasaki (JP)

(73) Assignee: Kabushiki Kaisha Toshiba, Minato-ku (JP)

( * ) Notice: Subject to any disclaimer, the term of this patent is extended or adjusted under 35 U.S.C. 154(b) by 0 days.

(21) Appl. No.: 15/912,598

(22) Filed: Mar. 6, 2018

(65) Prior Publication Data

US 2019/0083922 A1 Mar. 21, 2019

(30) Foreign Application Priority Data

Sep. 21, 2017 (JP) .................. 2017-181748
Feb. 28, 2018 (JP) .................. 2018-035256

(51) Int. Cl.
| | | |
|---|---|---|
| *C07C 211/08* | (2006.01) | |
| *B01D 53/14* | (2006.01) | |
| *C07C 309/14* | (2006.01) | |
| *C01B 32/50* | (2017.01) | |

(52) U.S. Cl.
CPC ..... B01D 53/1475 (2013.01); B01D 53/1425 (2013.01); B01D 53/1493 (2013.01); *B01D 2252/10* (2013.01); *B01D 2252/204* (2013.01); *B01D 2252/205* (2013.01); *B01D 2252/2056* (2013.01); *B01D 2252/20405* (2013.01); *B01D 2252/20436* (2013.01); *B01D 2252/20478* (2013.01); *B01D 2252/504* (2013.01); *B01D 2257/504* (2013.01); *C01B 32/50* (2017.08); *C07C 211/08* (2013.01); *C07C 309/14* (2013.01)

(58) Field of Classification Search
None
See application file for complete search history.

(56) References Cited

U.S. PATENT DOCUMENTS

| 9,056,271 B2 | 6/2015 | Kondo et al. |
| 2010/0011956 A1 | 1/2010 | Neumann et al. |
| 2010/0095851 A1 | 4/2010 | Hu |

(Continued)

FOREIGN PATENT DOCUMENTS

| EP | 0 134 948 A2 | 3/1985 |
| EP | 2 883 591 A1 | 6/2015 |

(Continued)

*Primary Examiner* — Daniel Berns
(74) *Attorney, Agent, or Firm* — Oblon, McClelland, Maier & Neustadt, L.L.P.

(57) ABSTRACT

A carbon dioxide absorbent of an embodiment includes a chain amine, a cyclic amine, and an acid. The chain amine is a compound expressed by Formula (1) of FIG. 1. $R^1$ in Formula (1) is hydrogen or an alkyl chain having at least one hydroxyl group and 1 to 7 carbon atoms. $R^2$ in Formula (1) is an alkyl chain having at least one hydroxyl group and 1 to 7 carbon atoms. $R^3$ in Formula (1) is hydrogen, a straight alkyl chain having 1 to 7 carbon atoms, a branched alkyl chain having 1 to 7 carbon atoms, or a cyclic alkyl chain having 5 to 7 carbon atoms.

9 Claims, 2 Drawing Sheets (1)

(2)

(3)

$R^{10}$—$SO_3H$ (4)

$HO_3S$—$R^{11}$—$SO_3H$ (5)

(56) References Cited

U.S. PATENT DOCUMENTS

| | | |
|---|---|---|
| 2011/0116997 A1 | 5/2011 | Attalla et al. |
| 2012/0161071 A1 | 6/2012 | Murai et al. |
| 2012/0308451 A1 | 12/2012 | Murai et al. |
| 2015/0093314 A1 | 4/2015 | Critchfield et al. |
| 2015/0110695 A1 | 4/2015 | Laroche et al. |
| 2015/0151246 A1 | 6/2015 | Murai et al. |
| 2016/0101385 A1 | 4/2016 | Mao et al. |
| 2016/0158690 A1* | 6/2016 | Puxty ................ B01D 53/1487 423/228 |
| 2016/0193568 A1 | 7/2016 | Fujimoto et al. |
| 2017/0266607 A1 | 9/2017 | Watando et al. |

FOREIGN PATENT DOCUMENTS

| | | |
|---|---|---|
| JP | 60-48116 | 3/1985 |
| JP | 2010-155753 | 7/2010 |
| JP | 2011-516244 | 5/2011 |
| JP | 2012-504043 | 2/2012 |
| JP | 2012-505077 | 3/2012 |
| JP | 2012-143744 | 8/2012 |
| JP | 2012-143745 | 8/2012 |
| JP | 2012-245483 | 12/2012 |
| JP | 2015-27647 A | 2/2015 |
| JP | 2015-71136 A | 4/2015 |
| JP | 2015-523203 | 8/2015 |
| JP | 2015-527189 | 9/2015 |
| JP | 2015-199007 | 11/2015 |
| JP | 2017-121610 | 7/2017 |
| JP | 2017-164696 | 9/2017 |

* cited by examiner (1)

(2)

(3)

$R^{10}-SO_3H$ (4)

$HO_3S-R^{11}-SO_3H$ (5)

CARBON DIOXIDE ABSORBENT AND APPARATUS OF SEPARATING AND RECOVERING CARBON DIOXIDE

CROSS-REFERENCE TO RELATED APPLICATION

This application is based upon and claims the benefit of priority from Japanese Patent Applications No. 2017-181748, filed on Sep. 21, 2017 and No. 2018-35256, filed on Feb. 28, 2018; the entire contents of which are incorporated herein by reference.

FIELD

Embodiments described herein relate to a carbon dioxide absorbent and an apparatus of separating and recovering carbon dioxide.

BACKGROUND

On the basis of a recent concern for global warming and strengthening of regulations, reduction of carbon dioxide emission from coal-fired power plants has been an urgent task. Therefore, as a method of reducing carbon dioxide emission, recovery of carbon dioxide by a chemical absorbent in addition to reduction of carbon dioxide emission by increasing efficiency of power plants is receiving great attention. As a specific absorbent, absorption by amines has been studied from the past. It is known that amine contained in a composition is dispersed by heating of a chemical absorption solution in a process of absorbing and emitting carbon dioxide using the chemical absorbent. Since there is a concern about an influence on a surrounding environment of a plant when a large amount of amine is dispersed in the air, an amine trap by water, an acid, or the like is installed.

DETAILED DESCRIPTION

A carbon dioxide absorbent of an embodiment includes a chain amine, a cyclic amine, and an acid. The chain amine is a compound expressed by Formula (1) of FIG. 1. $R^1$ in Formula (1) is hydrogen or an alkyl chain having at least one hydroxyl group and 1 to 7 carbon atoms. $R^2$ in Formula (1) is an alkyl chain having at least one hydroxyl group and 1 to 7 carbon atoms. $R^3$ in Formula (1) is hydrogen, a straight alkyl chain having 1 to 7 carbon atoms, a branched alkyl chain having 1 to 7 carbon atoms, or a cyclic alkyl chain having 5 to 7 carbon atoms.

The carbon dioxide absorbent according to an embodiment includes two kinds of amines and an acid. The carbon dioxide absorbent according to the embodiment includes a chain amine, a cyclic amine, and an acid. The carbon dioxide absorbent according to the embodiment is in a liquid state. Here, the liquid state means that the carbon dioxide absorbent is a liquid at 20° C. and 1 atm.

Figure 1:
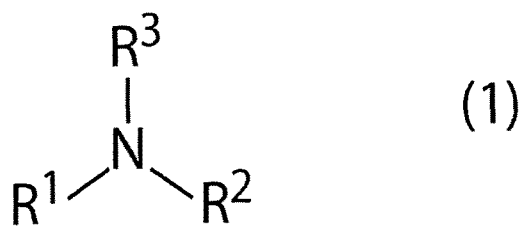
FIG. 1 shows structural formulas included in a carbon dioxide absorbent according to an embodiment.
Figure 1:
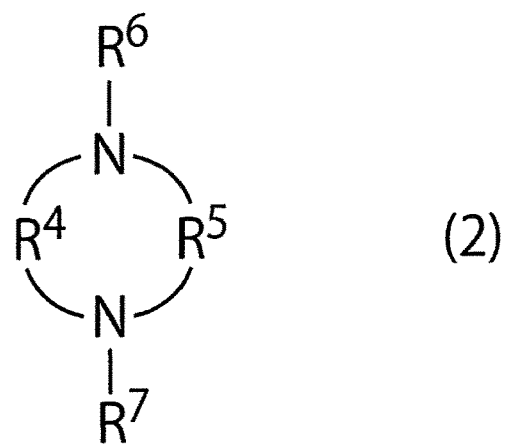
Figure 1:
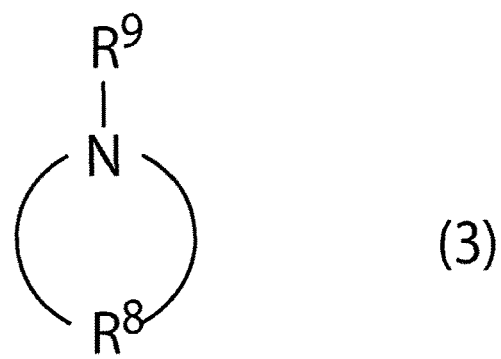

The chain amine according to the embodiment is a compound expressed by Formula (1) of FIG. 1. The chain amine may be any one of straight chain amines and branched amines. In the chain amine, a carbon skeleton including the amine does not have a cyclic structure. A straight line and a curve in the Formula represent a bond.

$R^1$ in Formula (1) is hydrogen or an alkyl chain having at least one hydroxyl group and 1 to 7 carbon atoms. $R^2$ in Formula (1) is an alkyl chain having at least one hydroxyl group and 1 to 7 carbon atoms. $R^3$ in Formula (1) is hydrogen, a straight alkyl chain having 1 to 7 carbon atoms, a branched alkyl chain having 1 to 7 carbon atoms, or a cyclic alkyl chain having 5 to 7 carbon atoms.

Specific examples of the chain amine expressed by Formula (1) include one or more selected from the group consisting of monoethanol amine, 2-amino-1-propanol, 3-amino-1-propanol, 1-amino-2-propanol, 2-amino-1-butanol, 3-amino-1-butanol, 4-amino-1-butanol, 2-amino-2-methyl-1-propanol, 2-amino-2-ethyl-1-propanol, 2-methyl amino ethanol, 2-ethylaminoethanol, diethanol amine, hydroxy ethyl hydroxy propyl amine, dipropanolamine, isopropyl amino ethanol, 3-methyl amine-1, 2-propanediol, cyclo pentyl amino ethanol, cyclo hexyl amino ethanol, dimethyl amino ethanol, diethyl amino ethanol, N-methyl diethanol amine, N-ethyl diethanol amine, 3-(dimethyl amino)-1, 2-propanediol, and 2-{[2-(dimethyl amino) ethyl] methyl amino}ethanol.

It is practical that pH of the carbon dioxide absorbent before absorbing carbon dioxide is 9.5 or more to 10.8 or less.

The carbon dioxide absorbent according to the embodiment contains the acid, thereby making it possible to satisfy the above-mentioned pH range. Dispersion of the amine at the time of heating the carbon dioxide absorbent in a process of separating and recovering carbon dioxide can be suppressed by setting the pH of the carbon dioxide absorbent to be in the above-mentioned range. Dispersion of the cyclic amine can be suppressed by setting the pH of the carbon dioxide absorbent to be in the above-mentioned range. In the carbon dioxide absorbent according to the embodiment, even in the case where the pH is lowered, the carbon dioxide absorbent has excellent carbon dioxide absorption and release performance. When the acid according to the embodiment is not added to the carbon dioxide absorbent, the pH of the carbon dioxide absorbent before absorbing carbon dioxide is about 11 to 13, which is out of the above-mentioned pH range.

The pH of the carbon dioxide absorbent before absorbing carbon dioxide is measured by a pH meter (LAQUAact pH/ORP Meter D-72, manufactured by HORIBA, Ltd.).

It is practical that a molar ratio of the cyclic amine to the acid (moles of the cyclic amine:moles of the acid) is 1.0:0.1 or more to 1.0:1.9 or less. The carbon dioxide absorbent is adjusted so as to have the above-mentioned molar ratio. It can be considered that the cyclic amine and ionized acid interact with each other in a solution to raise a boiling point of the cyclic amine, thereby suppressing dispersion of the cyclic amine. In contrast, when the molar ratio of the cyclic amine to the acid is less than 1.0:0.1, the interaction between the cyclic amine and the ionized acid becomes weak. Further, since absorption of carbon dioxide by amine is caused by a neutralization reaction between amine and carbon dioxide, when the molar ratio of the cyclic amine to the acid is more than 1.0:1.9, the pH is excessively low, and the neutralization reaction, that is, absorption of carbon dioxide is inhibited.

Two kinds of amines are included in the carbon dioxide absorbent according to the embodiment. In the case in which the carbon dioxide absorbent includes only one kind of amine, carbon dioxide absorption and release efficiency is low. Carbon dioxide can be efficiently absorbed and released by combining the amines according to the embodiment.

The cyclic amine according to the embodiment is at least one compound selected from the group consisting of a compound expressed by Formula (2) of FIG. 1, a compound expressed by Formula (3) of FIG. 1, and a compound in which structures expressed by Formulas (2) and (3) of FIG. 1 are linked with each other by a carbon chain.

$R^4$ in Formula (2) is an alkyl chain having 1 to 3 carbon atoms, optionally has an organic group including nitrogen as a side chain, and optionally has a hydroxyl group as a side chain. $R^5$ in Formula (2) is an alkyl chain having 2 to 3 carbon atoms, optionally has an organic group including nitrogen as a side chain, and optionally has a hydroxyl group as a side chain. $R^6$ in Formula (2) is hydrogen or a straight or branched alkyl chain having 1 to 4 carbon atoms, and optionally has a hydroxyl group. $R^7$ in Formula (2) is hydrogen or a straight or branched alkyl chain having 1 to 4 carbon atoms, and optionally has a hydroxyl group. $R^8$ in Formula (3) is a straight alkyl chain having 4 to 7 carbon atoms, optionally has an organic group including nitrogen as a side chain, and optionally has a hydroxyl group. $R^9$ in Formula (3) is hydrogen or a straight or branched alkyl chain having 1 to 4 carbon atoms, and optionally has a hydroxyl group.

Specific examples of the amine expressed by Formulas (2) and (3) may include at least one selected from the group consisting of piperidine, piperazine, 1-methylpiperidine, 1-methyl piperazine, 2-methyl piperazine, 4-hydroxy ethyl piperazine, 1,4-bis(2-hydroxy ethyl) piperazine, 1,4-dimethyl piperazine, 4-hydroxypiperidine, 1,4-dihydroxy ethyl piperazine, 2-piperidineethanol, 3-piperidino-1,2-propanediol, 2-piperidinemethanol, 1-piperidinepropanol, 3-piperidinemethanol, homo piperazine, 1-(2-amino ethyl) piperazine, 1-(2-amino ethyl) piperidine, 4-(2-amino ethyl) morpholine, N-(3-amino propyl)-2-pipecoline, and N(3-amino propyl)morpholine.

The carbon dioxide absorbent includes a solvent in addition to the amine and the acid. It is practical that the total amount of the amines in the carbon dioxide absorbent is 20 mass % or more to 80 mass % or less. When the total amount of the amines contained in the carbon dioxide absorbent is less than 20 mass %, sufficient carbon dioxide absorption performance is not obtained. Further, when the total amount of the amines contained in the carbon dioxide absorbent is more than 80 mass %, operability and absorption performance may be deteriorated due to an increase in viscosity, and a sufficient effect is not obtained. From the same viewpoint, the total amount of the amines contained in the carbon dioxide absorbent is 30 mass % or more to 70 mass % or less, which is practical. In the case of using a mixed absorbent of two or more kinds of amines and water, mixing of the amines can be carried out at an arbitrary ratio within the above-mentioned amine concentration range.

A quantitative and qualitative analysis method performed on total amines contained in the carbon dioxide absorbent is not particularly limited as long as the method can perform quantitative and qualitative analysis of amines. For example, the quantitative and qualitative analysis of total amines may be performed using high performance liquid chromatography (HPLC), liquid chromatography/mass spectrometry (LC/MS), liquid chromatography/tandem mass spectrometry (LC/MS/MS), liquid chromatography/time-of-flight mass spectrometry (LC/TOF-MS), gas chromatography/mass spectrometry (GC/MS), gas chromatography/tandem mass spectrometry (GC/MS/MS), gas chromatography/time-of-flight mass spectrometry (GC/TOF-MS), ion chromatography (IC), ion chromatography/mass chromatography (IC/MS), 1H nuclear magnetic resonance (1H-NMR), 13C magnetic resonance (13C-NMR), or the like.

Examples of the acid may include at least one selected from the group consisting of hydrochloric acid, phosphoric acid, sulfuric acid, nitric acid, hydroiodic acid, acetic acid, citric acid, formic acid, propionic acid, butanoic acid, methylpropionic acid, pentanoic acid, 2,2-dimethylpropionic acid, benzoic acid, phenylacetic acid, gluconic acid, lactic acid, oxalic acid, tartaric acid, and an organic acid having a sulfo group, and the like. Further, in the case of using formic acid as the acid, degradation of the carbon dioxide absorbent may easily occur. Therefore, in consideration of degradation of the carbon dioxide absorbent, it is practical that the acid is at least one selected from the group consisting of hydrochloric acid, phosphoric acid, sulfuric acid, nitric acid, hydroiodic acid, acetic acid, citric acid, propionic acid, butanoic acid, methylpropionic acid, pentanoic acid, 2,2-dimethylpropionic acid, benzoic acid, phenylacetic acid, gluconic acid, lactic acid, oxalic acid, tartaric acid, and an organic acid having a sulfo group, and the like.

The kind of acid is specified by ion chromatography or high performance liquid chromatography (HPLC).

In view of suppressing diffusion of amine, it is practical that an amount of an acid which is hard to be ionized in the carbon dioxide absorbent according to the embodiment is small. Therefore, it is preferable that an acid having pKa of 6.0 or less is contained in the carbon dioxide absorbent. Examples of the acid having pKa of 6.0 or less include at least one selected from the group consisting of hydrochloric acid, phosphoric acid, sulfuric acid, nitric acid, hydroiodic acid, acetic acid, citric acid, formic acid, propionic acid, butanoic acid, methylpropionic acid, pentanoic acid, 2,2-dimethylpropionic acid, benzoic acid, phenylacetic acid, chloroethanoic acid, dichloroethanoic acid, trichloroethanoic acid, fluoroethanoic acid, bromoethanoic acid, iodoethanoic acid, gluconic acid, lactic acid, oxalic acid, tartaric acid, and an organic acid having a sulfo group. Therefore, in consideration of degradation of the carbon dioxide absorbent, it is practical that the acid which is hard to be ionized is at least one selected from the group consisting of hydrochloric acid, phosphoric acid, sulfuric acid, nitric acid, hydroiodic acid, acetic acid, citric acid, propionic acid, butanoic acid, methylpropionic acid, pentanoic acid, 2,2-dimethylpropionic acid, benzoic acid, phenylacetic acid, chloroethanoic acid, dichloroethanoic acid, trichloroethanoic acid, fluoroethanoic acid, bromoethanoic acid, iodoethanoic acid, gluconic acid, lactic acid, oxalic acid, tartaric acid, and an organic acid having a sulfo group.

It is more practical that the acid includes an organic acid having a sulfo group, expressed by Formula (4) illustrated in FIG. 1; an organic acid having a sulfo group, expressed by Formula (5); or an organic acid having a sulfo group, expressed by Formula (4) and an organic acid having a sulfo group, expressed by Formula (5). Since these acids have low vapor pressures, large molecular weights, and small pKa(s), these acids contribute to suppressing dispersion of amine. There is a case of using perfluorosulfonic acid as a $CO_2$ absorbent, but since an alkyl sulfonic acid structure has low corrosiveness, the alkyl sulfonic acid structure is practical.

$R^{10}$ in Formula (4) is an organic group including an alkyl group, an aryl group, or an alkyl group and an aryl group, optionally including an amino group, a hydroxyl group, or an amino group and a hydroxyl group, and having a straight chain structure with 1 to 5 carbon atoms in the straight chain or a branched structure. $R^{11}$ in Formula (5) is an organic group having an alkyl group, or an amino group and an alkyl group, and having 2 to 5 carbon atoms in a straight chain.

Specific examples of the acid having any one or both of the sulfo groups in Formulas (4) and (5) include at least one selected from the group consisting of methane sulfonic acid, ethane sulfonic acid, propane sulfonic acid, 1,2-ethane disulfonic acid, 1,3-propanedisulfonic acid, 2-amino ethane sulfonic acid, N,N-bis(2-hydroxyethyl)-2-amino ethane sulfonic acid, 2,2-iminobis-ethane sulfonic acid, 2-dimethyl amino ethane sulfonic acid, and 3-dimethyl amino-1-propane sulfonic acid.

The carbon dioxide absorbent may contain other components such as a deterioration inhibitor, an antifoaming agent, a viscosity modifier, and an antioxidant, in addition to the above-mentioned components. The carbon dioxide absorbent is not slurry but a solution. A carbon dioxide absorbent solution has a solid content concentration of 5 mass % or less and viscosity of 3000 mPa·s or less.

When alkali earth metals such as Ca or Mg are added to the carbon dioxide absorbent, these alkali earth metals react with carbon dioxide to produce precipitating compounds such as $CaCO_3$. Therefore, except for unavoidable trace amounts of ions contained in water, the alkali earth metal such as Ca or Mg is not included in the carbon dioxide absorbent. That is, a concentration of the alkali earth metal (ion) unavoidably included before absorption of carbon dioxide, except for ingredients derived from exhaust gas and ingredients eluted from equipment, and the like, is 1 wt % or less.

<Method of Separating and Recovering Carbon Dioxide>

In a method of separating and recovering carbon dioxide according to the present embodiment, carbon dioxide is separated and recovered from gas containing carbon dioxide by contacting the gas containing carbon dioxide with a carbon dioxide unabsorbed carbon dioxide absorbent (the carbon dioxide absorbent according to previous embodiment) before absorbing carbon dioxide from the gas containing carbon dioxide according to the embodiment described above.

The method of separating and recovering carbon dioxide includes: (a) a process of absorbing carbon dioxide in the carbon dioxide unabsorbed carbon dioxide absorbent and obtaining a carbon dioxide absorbed carbon dioxide absorbent; and (b) a process of separating carbon dioxide from the carbon dioxide absorbed carbon dioxide absorbent which has absorbed carbon dioxide. In the process (a) of absorbing carbon dioxide, carbon dioxide is absorbed in the carbon dioxide unabsorbed carbon dioxide absorbent by contacting a carbon dioxide-containing exhaust gas with the carbon dioxide unabsorbed carbon dioxide absorbent. Further, in the process (b) of separating carbon dioxide, carbon dioxide is desorbed by heating the carbon dioxide absorbed carbon dioxide absorbent which has absorbed carbon dioxide obtained in the above-described process (a) of absorbing carbon dioxide. The desorbed carbon dioxide may be recovered, such that treatment such as storage, decomposition, or the like, of the carbon dioxide can be performed.

In the process (a) of absorbing carbon dioxide, a method of contacting the gas containing carbon dioxide with an aqueous solution containing the above-described carbon dioxide absorbent is not particularly limited. In the process (a) of absorbing carbon dioxide, for example, a method of bubbling the gas containing carbon dioxide in the carbon dioxide absorbent so as to be absorbed, a method of dropping the carbon dioxide absorbent in a mist form in a gas flow containing carbon dioxide (an atomizing or spraying method), a method of allowing the gas containing carbon dioxide and the carbon dioxide absorbent to come in countercurrent contact with each other in an absorption tower containing a filler made of a porcelain material or metal mesh, or the like, may be used.

In the process (a) of absorbing carbon dioxide, it is practical that at the time of absorbing the gas containing carbon dioxide in the aqueous solution, a temperature of the carbon dioxide absorbent is generally in a range of room temperature to 60° C. or less. The process of absorbing carbon dioxide is more practically performed at 50° C. or less, more specifically, about 20 to 45° C. The lower the temperature at which the process of absorbing carbon dioxide is performed, the larger the absorption amount of carbon dioxide, but a lower limit value of a treatment temperature is determined by a temperature of the gas, a heat recovery target, or the like in the process. Absorption of carbon dioxide is generally performed at approximately atmospheric pressure. Although it is possible to pressurize to a higher pressure to improve absorption performance, it is practical that absorption of carbon dioxide is performed at the atmospheric pressure to suppress energy consumption required for compression.

Here, a saturated absorption amount of carbon dioxide is a value obtained by measuring an amount of inorganic carbon in the carbon dioxide absorbent using an infrared (IR) type gas concentration meter. Further, an absorption rate of carbon dioxide is a value measured using an infrared type carbon dioxide meter after 2 minutes from the start of absorption of carbon dioxide.

In the process (b) of separating carbon dioxide, as a method of separating carbon dioxide from the carbon dioxide absorbent which has absorbed carbon dioxide and recovering pure or high-concentration carbon dioxide, a method of heating the carbon dioxide absorbent similarly to distillation and foaming in a kettle to desorb carbon dioxide, a method of heating the carbon dioxide absorbent in a plate tower, a spray tower, or a regeneration tower containing a filler made of a porcelain material or a metal mesh, while increasing a liquid interface, or the like, may be used. As a result, carbon dioxide is separated and released from carbamic acid anions or bicarbonate ions.

In the process (b) of separating carbon dioxide, a temperature of the carbon dioxide absorbent at the time of separating carbon dioxide is generally 70° C. or more and for example, 80° C. or more, or about 90° C. to 120° C. The temperature of the carbon dioxide absorbent at the time of separating carbon dioxide is practically 80° C. or more, and more practically about 90 to 120° C. The higher the temperature, the larger the absorption amount, but in the case of increasing the temperature, energy required to heat the absorption solution is increased. Therefore, the temperature of the carbon dioxide absorbent at the time of separating carbon dioxide is determined by the temperature of the gas, the heat recovery target, or the like in the process. It is practical that a pressure at the time of desorbing carbon dioxide is generally 0.1 to 0.5 MPa, and practically, about 0.1 to 0.2 MPa (absolute pressure).

The carbon dioxide absorbent after separating carbon dioxide is returned to and circulated and used (recycled) again in the process of absorbing carbon dioxide. Here, heat supplied at the time of release of carbon dioxide is generally heat-exchanged to thereby be cooled in a heat exchanger in order to pre-heat the carbon dioxide absorbent injected into the regeneration tower during a process of recycling the carbon dioxide absorbent.

Purity of the carbon dioxide recovered as described above is generally about 95 to 99 vol %, which is significantly high. This pure carbon dioxide or high-concentration carbon dioxide is used as a synthesis raw material of a chemical or a polymer material, a cooling agent for freezing food, or the like. In addition, the recovered carbon dioxide may also be separated and stored in a basement or the like, using methods being currently developed.

The largest energy is consumed in the process of separating carbon dioxide from the carbon dioxide absorbent to regenerate the carbon dioxide absorbent (the process of separating carbon dioxide) among the above-mentioned processes. In this process of separating carbon dioxide, about 50 to 80% of the energy in the entire process is consumed. Therefore, cost in the processes of absorbing and separating carbon dioxide can be decreased by reducing energy consumed in the process of separating carbon dioxide in which the carbon dioxide absorbent is regenerated. This makes it possible to economically advantageously perform the separation and recovery of carbon dioxide from the exhaust gas.

According to the present embodiment, energy required in the process of separating carbon dioxide (regeneration process) can be decreased by using the carbon dioxide absorbent according to the above-described embodiment. Therefore, the process of absorbing and separating carbon dioxide can be performed under economically advantageous conditions.

Further, an amine compound (1) according to the embodiment described above has lower corrosivity toward metal materials such as carbon steel, as compared to alkanol amines such as monoethanol amine conventionally used as a carbon dioxide absorbent. Therefore, for example, the necessity to use a high-cost high-grade corrosion-resistant steel at the time of constructing a plant is decreased by adopting the method of separating and recovering carbon dioxide using the carbon dioxide absorbent according to the present embodiment, which is advantageous in view of cost.

<Apparatus of Separating and Recovering Carbon Dioxide>

An apparatus of separating and recovering carbon dioxide according to the present embodiment includes: an absorption tower separating and recovering carbon dioxide from gas containing carbon dioxide by contacting the gas containing carbon dioxide with a carbon dioxide unabsorbed carbon dioxide absorbent (the carbon dioxide absorbent according to previous embodiment) to allow carbon dioxide to be absorbed in the carbon dioxide unabsorbed carbon dioxide absorbent and obtaining a carbon dioxide absorbed carbon dioxide; and a regeneration tower regenerating the carbon dioxide absorbed carbon dioxide absorbent by desorbing carbon dioxide from the carbon dioxide absorbed carbon dioxide absorbent which has absorbed the carbon dioxide absorbed carbon dioxide absorbent.

Figure 2:
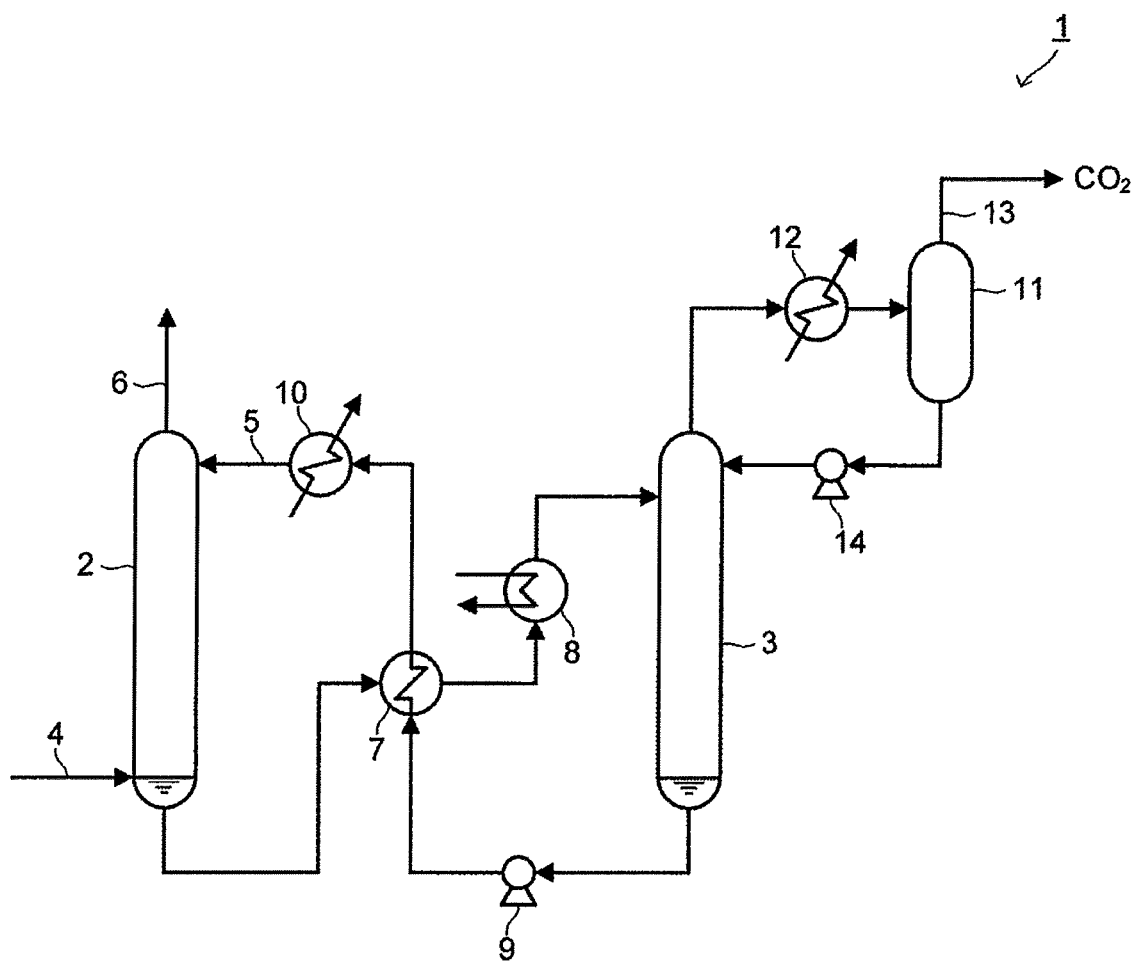
FIG. 2 is a schematic view of an apparatus of separating and recovering carbon dioxide according to the embodiment.

FIG. 2 is a schematic view of the apparatus of separating and recovering carbon dioxide according to the embodiment.

An apparatus 1 of separating and recovering carbon dioxide includes an absorption tower 2 and a regeneration tower 3. In the apparatus 1 of separating and recovering carbon dioxide, the absorption tower 2 separates and recovers carbon dioxide by contacting gas containing carbon dioxide (hereinafter, referred to as "exhaust gas") with a carbon dioxide absorbent and absorbing carbon dioxide from this exhaust gas. In the apparatus 1 of separating and recovering carbon dioxide, the regeneration tower 3 separates carbon dioxide from the carbon dioxide absorbent which has absorbed carbon dioxide in the absorption tower 2, and regenerates the carbon dioxide absorbent.

As illustrated in FIG. 2, the exhaust gas containing carbon dioxide such as combustion exhaust gas discharged from a thermal power plant, or the like, passes through a gas supply hole 4 to thereby be induced to a lower portion of the absorption tower 2. The carbon dioxide absorbent is supplied from a carbon dioxide absorbent supply hole 5 at an upper portion of the absorption tower 2 to thereby be accommodated in the absorption tower 2. The exhaust gas induced to the absorption tower 2 comes in contact with the carbon dioxide absorbent accommodated in the absorption tower 2. As the carbon dioxide absorbent, the carbon dioxide absorbent according to the embodiment described above is used.

It is practical that a pH value of the carbon dioxide absorbent is adjusted to at least 9 or more. It is practical that an optimal pH value of the carbon dioxide absorbent is appropriately selected depending on the kind, a concentration, a flow rate, or the like of harmful gas contained in the exhaust gas. In addition, the carbon dioxide absorbent can contain other compounds such as a nitrogen-containing compound improving carbon dioxide absorption performance, an antioxidant, a pH adjuster, and the like, in an arbitrary ratio.

As described above, the exhaust gas comes in contact with the carbon dioxide absorbent in the absorption tower 2, such that carbon dioxide in the exhaust gas is absorbed in the carbon dioxide absorbent to thereby be separated and recovered from the exhaust gas. The exhaust gas after carbon dioxide is separated and recovered therefrom is discharged to the outside of the absorption tower 2 from a gas discharge hole 6.

The carbon dioxide absorbent which has absorbed carbon dioxide is sequentially transferred from the absorption tower 2 to a heat exchanger 7 and a heater 8 so as to be heated, and then transferred to the regeneration tower 3. The carbon dioxide absorbent transferred into the regeneration tower 3 is moved from an upper portion of the regeneration tower 3 to a lower portion thereof, and while the carbon dioxide absorbent is moved, carbon dioxide in the carbon dioxide absorbent is released, and the carbon dioxide absorbent is regenerated.

The carbon dioxide absorbent regenerated in the regeneration tower 3 is sequentially transferred to the heat exchanger 7 and an absorption solution cooler 10 by a pump 9, and is returned from the carbon dioxide absorbent supply hole 5 to the absorption tower 2.

Meanwhile, carbon dioxide separated from the carbon dioxide absorbent comes in contact with reflux water supplied from a reflux drum 11 in the upper portion of the regeneration tower 3 to thereby be discharged to the outside of the regeneration tower 3. The reflux water in which carbon dioxide is dissolved is cooled in a reflux condenser 12 and separated from a liquid component in which water vapor accompanied with carbon dioxide is condensed in the reflux drum 11. This liquid component is induced to the process of recovering carbon dioxide by a recovery carbon dioxide line 13. Meanwhile, the reflux water from which carbon dioxide is separated is transferred to the regeneration tower 3 by a reflux water pump 14.

With the apparatus 1 of separating and recovering carbon dioxide according to the present embodiment, it is possible to efficiently separate and recover carbon dioxide by using the carbon dioxide absorbent having excellent operability, absorption characteristics, and desorption characteristics of carbon dioxide.

Hereinafter, the carbon dioxide absorbent according to the embodiment will be described in more detail through Examples.

Comparative Example 1

A carbon dioxide absorbent including N-ethyl diethanol amine as a chain amine and piperazine as a cyclic amine was prepared. No acid was added to the carbon dioxide absorbent of Comparative Example 1. A mass ratio of N-ethyl diethanol amine and piperazine was 5:1 (N-ethyl diethanol amine: piperazine). A pH of the prepared carbon dioxide absorbent was 12.3. Then, a mixed gas of carbon dioxide and nitrogen gas was bubbled in the carbon dioxide absorbent, and an absorption equilibrium amount of carbon dioxide was measured at 40° C. and 70° C. Further, after measurement of the absorption equilibrium amount of carbon dioxide, an amount of the cyclic amine in the carbon dioxide absorbent was measured.

Example 1

A carbon dioxide absorbent was prepared by mixing N-ethyl diethanol amine as a chain amine, piperazine as a cyclic amine, and sulfuric acid. The carbon dioxide absorbent was prepared in a similar manner to Comparative Example 1 except that a molar ratio of sulfuric acid to piperazine was 0.6 (the number of moles of sulfuric acid/the number of moles of piperazine). A pH of the obtained carbon dioxide absorbent was 10.5. Then, an absorption equilibrium amount of carbon dioxide was measured at 40° C. and 70° C., as in Comparative Example 1. A difference between the absorption equilibrium amounts of carbon dioxide at 40° C. and 70° C. was calculated, and a ratio of a recovery amount of carbon dioxide to that in Comparative Example 1 in which the acid was not added was calculated. The absorption amount of carbon dioxide in Example 1 was 84% of the absorption amount of carbon dioxide in Comparative Example 1. Further, a residual amount of piperazine as the cyclic amine in the carbon dioxide absorbent after measurement of the absorption equilibrium amount of carbon dioxide was larger than that in Comparative Example 1. Since the carbon dioxide absorbent used sulfuric acid as the acid, in view of prevention of degradation of the carbon dioxide absorbent, the results in Example 1 were preferable.

Example 2

A carbon dioxide absorbent was prepared in a similar manner to Example 1 except that a ratio of sulfuric acid was changed. A molar ratio of sulfuric acid to piperazine was 1.4 (the number of moles of sulfuric acid/the number of moles of piperazine). A pH of the prepared carbon dioxide absorbent was 10.3. Then, a difference between the absorption equilibrium amounts of carbon dioxide at 40° C. and 70° C. was calculated and a ratio of a recovery amount of carbon dioxide to that in Comparative Example 1 in which the acid was not added was calculated, as in Example 1. The absorption amount of carbon dioxide in Example 2 was 86% of the absorption amount of carbon dioxide in Comparative Example 1. Further, a residual amount of piperazine as a cyclic amine in the carbon dioxide absorbent after measurement of the recovery amount of carbon dioxide was larger than those in Comparative Example 1 and Example 1. Since the carbon dioxide absorbent used sulfuric acid as the acid, in view of prevention of degradation of the carbon dioxide absorbent, the results in Example 2 were preferable.

Comparative Example 2

A carbon dioxide absorbent was prepared in a similar manner to Example 1 except that a ratio of sulfuric acid was changed. A molar ratio of sulfuric acid to piperazine was 2.0 (the number of moles of sulfuric acid/the number of moles of piperazine). A pH of the obtained carbon dioxide absorbent was 9.4. Then, a difference between the absorption equilibrium amounts of carbon dioxide at 40° C. and 70° C. was calculated and a ratio of a recovery amount of carbon dioxide to that in Comparative Example 1 in which the acid was not added was calculated, as in Example 1. The absorption amount of carbon dioxide in Comparative Example 2 was 73% of the absorption amount of carbon dioxide in Comparative Example 1. Further, a residual amount of piperazine as a cyclic amine in the carbon dioxide absorbent after measurement of the recovery amount of carbon dioxide was larger than those in Comparative Example 1 and Example 1.

Comparative Example 3

A carbon dioxide absorbent was prepared by mixing diethanol amine as a chain amine and 1-methyl piperazine as a cyclic amine with each other. An acid was not added to the carbon dioxide absorbent in Comparative Example 3. A mass ratio of diethanol amine and 1-methyl piperazine was 5:1 (diethanol amine: 1-methyl piperazine). A pH of the obtained carbon dioxide absorbent was 12.0. Then, an absorption equilibrium amount of carbon dioxide was measured at 40° C. and 70° C., as in Comparative Example 1. Further, after measurement of the absorption equilibrium amount of carbon dioxide, an amount of the cyclic amine in the carbon dioxide absorbent was measured.

Example 3

A carbon dioxide absorbent was prepared by mixing diethanol amine as a chain amine, 1-methyl piperazine as a cyclic amine, and hydrochloric acid with each other. The carbon dioxide absorbent was prepared in a similar manner to Comparative Example 3 except that a molar ratio of hydrochloric acid to 1-methyl piperazine was 0.3 (the number of moles of hydrochloric acid/the number of moles of 1-methyl piperazine). A pH of the obtained carbon dioxide absorbent was 10.7. Then, an absorption equilibrium amount of carbon dioxide was measured at 40° C. and 70° C., as in Comparative Example 1. A difference between the absorption equilibrium amounts of carbon dioxide at 40° C. and 70° C. was calculated, and a ratio of a recovery amount of carbon dioxide to that in Comparative Example 2 in which the acid was not added was calculated. The absorption amount of carbon dioxide in Example 3 was 95° of the absorption amount of carbon dioxide in Comparative Example 3. Further, a residual amount of 1-methyl piperazine as the cyclic amine in the carbon dioxide absorbent after measurement of the absorption equilibrium amount of carbon dioxide was larger than that in Comparative Example 2. Since hydrochloric acid was used as the acid, in view of prevention of degradation of the carbon dioxide absorbent, the results in Example 3 were preferable.

Example 4

A carbon dioxide absorbent was prepared in a similar manner to Example 3 except that a ratio of hydrochloric acid was changed. A molar ratio of hydrochloric acid to 1-methyl piperazine was 1.4 (the number of moles of hydrochloric acid/the number of moles of 1-methyl piperazine). A pH of the obtained carbon dioxide absorbent was 10.1. Then, a difference between the absorption equilibrium amounts of carbon dioxide at 40° C. and 70° C. was calculated and a ratio of a recovery amount of carbon dioxide to that in Comparative Example 1 in which the acid was not added was calculated, as in Example 1. The absorption amount of carbon dioxide in Example 4 was 82% of the absorption amount of carbon dioxide in Comparative Example 3. Further, a residual amount of 1-methyl piperazine as a cyclic amine in the carbon dioxide absorbent after measurement of the recovery amount of carbon dioxide was larger than those in Comparative Example 3 and Example 3. Since hydrochloric acid was used as the acid, in view of prevention of degradation of the carbon dioxide absorbent, the results in Example 4 were preferable.

Example 5

A carbon dioxide absorbent was prepared in a similar manner to Example 3 except that a ratio of hydrochloric acid was changed. A molar ratio of hydrochloric acid to 1-methyl piperazine was 1.0 (the number of moles of hydrochloric acid/the number of moles of 1-methyl piperazine). A pH of the obtained carbon dioxide absorbent was 9.9. Then, a difference between the absorption equilibrium amounts of carbon dioxide at 40° C. and 70° C. was calculated and a ratio of a recovery amount of carbon dioxide to that in Comparative Example 1 in which the acid was not added was calculated, as in Example 1. The absorption amount of carbon dioxide in Example 5 was 83% of the absorption amount of carbon dioxide in Comparative Example 3. Further, a residual amount of 1-methyl piperazine as a cyclic amine in the carbon dioxide absorbent after measurement of the recovery amount of carbon dioxide was larger than those in Comparative Example 3 and Examples 3 and 4. Since hydrochloric acid was used as the acid, in view of prevention of degradation of the carbon dioxide absorbent, the results in Example 5 were preferable.

Example 6

A carbon dioxide absorbent was prepared in a similar manner to Example 3 except that a ratio of hydrochloric acid was changed. A molar ratio of hydrochloric acid to 1-methyl piperazine was 1.4 (the number of moles of hydrochloric acid/the number of moles of 1-methyl piperazine). A pH of the obtained carbon dioxide absorbent was 9.6. Then, a difference between the absorption equilibrium amounts of carbon dioxide at 40° C. and 70° C. was calculated and a ratio of a recovery amount of carbon dioxide to that in Comparative Example 1 in which the acid was not added was calculated, as in Example 1. The absorption amount of carbon dioxide in Example 6 was 86° of the absorption amount of carbon dioxide in Comparative Example 3. Further, a residual amount of 1-methyl piperazine as a cyclic amine in the carbon dioxide absorbent after measurement of the recovery amount of carbon dioxide was larger than those in Comparative Example 3 and Examples 3, 4, and 5. Since hydrochloric acid was used as the acid, in view of prevention of degradation of the carbon dioxide absorbent, the results in Example 6 were preferable.

Comparative Example 4

A carbon dioxide absorbent was prepared in a similar manner to Example 3 except that a ratio of hydrochloric acid was changed using 1-methyl piperazine as a cyclic amine. A molar ratio of hydrochloric acid to 1-methyl piperazine was 2.0 (the number of moles of hydrochloric acid/the number of moles of 1-methyl piperazine). A pH of the obtained carbon dioxide absorbent was 9.0. Then, a difference between absorption equilibrium amounts of carbon dioxide at 40° C. and 70° C. was calculated as in Example 1, and a ratio of a recovery amount of carbon dioxide to that in Comparative Example 3 in which the acid was not added was calculated. The absorption amount of carbon dioxide in Comparative Example 4 was 70° of the absorption amount of carbon dioxide in Comparative Example 2. Further, a residual amount of the cyclic amine in the carbon dioxide absorbent after measurement of the recovery amount of carbon dioxide was larger than those in Comparative Example 3 and Examples 3, 4 and 5.

Comparative Example 5

A carbon dioxide absorbent was prepared by mixing dimethyl ethanol amine as a chain amine and 2-methyl piperazine as a cyclic amine with each other. An acid was not added to the carbon dioxide absorbent in Comparative Example 5. A mass ratio of dimethyl ethanol amine and 2-methyl piperazine was 5:1 (dimethyl ethanol amine: 2-methyl piperazine). A pH of the obtained carbon dioxide absorbent was 12.4. Then, an absorption equilibrium amount of carbon dioxide was measured at 40° C. and 70° C., as in Comparative Example 1. Further, after measurement of the absorption equilibrium amount of carbon dioxide, an amount of the cyclic amine in the carbon dioxide absorbent was measured.

Example 7

A carbon dioxide absorbent was prepared by mixing dimethyl ethanol amine as a chain amine, 2-methyl piperazine as a cyclic amine, and formic acid with one another. The carbon dioxide absorbent was prepared in a similar manner to Comparative Example 3 except that a molar ratio of formic acid to 2-methyl piperazine was 0.3 (the number of moles of formic acid/the number of moles of 2-methyl piperazine). A pH of the obtained carbon dioxide absorbent was 10.2. Then, an absorption equilibrium amount of carbon dioxide was measured at 40° C. and 70° C., as in Comparative Example 3. A difference between absorption equilibrium amounts of carbon dioxide at 40° C. and 70° C. was calculated, and a ratio of a recovery amount of carbon dioxide to that in Comparative Example 5 in which the acid was not added was calculated. The absorption amount of carbon dioxide in Example 7 was 97° of the absorption amount of carbon dioxide in Comparative Example 3. Further, a residual amount of 2-methyl piperazine as the cyclic amine in the carbon dioxide absorbent after measurement of the absorption equilibrium amount of carbon dioxide was larger than that in Comparative Example 5.

Example 8

A carbon dioxide absorbent was prepared in a similar manner to Example 7 except that a ratio of formic acid was changed. A molar ratio of formic acid to 2-methyl piperazine was 1.0 (the number of moles of formic acid/the number of moles of 2-methyl piperazine). A pH of the obtained carbon dioxide absorbent was 9.5. Then, a difference between absorption equilibrium amounts of carbon dioxide at 40° C. and 70° C. was calculated as in Example 1, and a ratio of a recovery amount of carbon dioxide to that in Comparative Example 5 in which the acid was not added was calculated. The absorption amount of carbon dioxide in Example 8 was 82% of the absorption amount of carbon dioxide in Comparative Example 2. Further, a residual amount of 2-methyl piperazine as a cyclic amine in the carbon dioxide absorbent after measurement of the recovery amount of carbon dioxide was larger than those in Comparative Example 5 and Example 7.

Comparative Example 6

A carbon dioxide absorbent was prepared in a similar manner to Example 7 except that formic acid with dimethyl ethanol amine as a chain amine and 2-methyl piperazine as a cyclic amine were mixed with each other to change a ratio of formic acid. A molar ratio of formic acid to hydroxyl piperazine was 2.0 (the number of moles of formic acid/the number of moles of hydroxyl piperazine). A pH of the obtained carbon dioxide absorbent was 8.8. Then, a difference between absorption equilibrium amounts of carbon dioxide at 40° C. and 70° C. was calculated as in Example 1, and a ratio of a recovery amount of carbon dioxide to that in Comparative Example 1 in which the acid was not added was calculated. The absorption amount of carbon dioxide in Comparative Example 6 was 67% of the absorption amount of carbon dioxide in Comparative Example 2. Further, a residual amount of the cyclic amine in the carbon dioxide absorbent after measurement of the recovery amount of carbon dioxide was larger than those in Comparative Example 5 and Examples 7 and 8.

Comparative Example 7

A carbon dioxide absorbent was prepared by mixing triethanol amine as a chain amine and hydroxyethyl piperazine as a cyclic amine with each other. An acid was not added to the carbon dioxide absorbent in Comparative Example 7. A mass ratio of triethanol amine and hydroxyethyl piperazine was 5:1 (triethanol amine:hydroxyethyl piperazine). A pH of the obtained carbon dioxide absorbent was 12.5. Then, an absorption equilibrium amount of carbon dioxide was measured at 40° C. and 70° C., as in Comparative Example 1. Further, after measurement of the absorption equilibrium amount of carbon dioxide, an amount of the cyclic amine in the carbon dioxide absorbent was measured.

Example 9

A carbon dioxide absorbent was prepared by mixing triethanol amine as a chain amine, hydroxyethyl piperazine as a cyclic amine, and ethanedisulfonic acid dihydrate with one another. The carbon dioxide absorbent was prepared in a similar manner to Comparative Example 3 except that a molar ratio of ethanedisulfonic acid dihydrate to 2-methyl piperazine was 0.6 (the number of moles of ethanedisulfonic acid dihydrate/the number of moles of 2-methyl piperazine). A pH of the prepared carbon dioxide absorbent was 10.3. Then, an absorption equilibrium amount of carbon dioxide was measured at 40° C. and 70° C., as in Comparative Example 3. A difference between absorption equilibrium amounts of carbon dioxide at 40° C. and 70° C. was calculated, and a ratio of a recovery amount of carbon dioxide to that in Comparative Example 5 in which the acid was not added was calculated. The absorption amount of carbon dioxide in Example 9 was 85% of the absorption amount of carbon dioxide in Comparative Example 7. Further, a residual amount of hydroxyethyl piperazine as the cyclic amine in the carbon dioxide absorbent after measurement of the absorption equilibrium amount of carbon dioxide was larger than that in Comparative Example 7. Since ethanedisulfonic acid dihydrate was used as the acid, in view of prevention of degradation of the carbon dioxide absorbent, the results in Example 9 were preferable.

Comparative Example 8

A carbon dioxide absorbent was prepared in a similar manner to Example 1 except that a ratio of ethanedisulfonic acid was changed. A molar ratio of ethanedisulfonic acid to hydroxyethyl piperazine was 2.0 (the number of moles of ethanedisulfonic acid/the number of moles of hydroxyethyl piperazine). A pH of the obtained carbon dioxide absorbent was 9.2. Then, a difference between absorption equilibrium amounts of carbon dioxide at 40° C. and 70° C. was calculated as in Example 1, and a ratio of a recovery amount of carbon dioxide to that in Comparative Example 1 in which the acid was not added was calculated. The absorption amount of carbon dioxide in Comparative Example 8 was 71% of the absorption amount of carbon dioxide in Comparative Example 7. Further, a residual amount of hydroxyethyl piperazine as a cyclic amine in the carbon dioxide absorbent after measurement of the recovery amount of carbon dioxide was larger than those in Comparative Example 1 and Example 1.

From the results of Examples 1 to 9, volatilization of the cyclic amine was suppressed in a state in which the recovery amount of $CO_2$ was maintained by setting an addition amount of the acid to be 0.1 to 1.9 or less (molar ratio) with respect to the cyclic amine. As the addition amount of the acid to the cyclic amine was increased within the above-mentioned range, volatilization of the cyclic amine was further suppressed. Comparing Comparative Example 1 and Example 1, the recovery amount of carbon dioxide in Comparative Example 1 was larger than that in Example 1 at the time of performing a process of recovering carbon dioxide once (one cycle). However, since the cyclic amine in the carbon dioxide absorbent was mostly lost in Comparative Example 1, in the case of continuously performing a process of absorbing and releasing carbon dioxide several times, the recovery amount of carbon dioxide in Example 1 was increased. In order to perform the process of absorbing and releasing carbon dioxide several times in Comparative Example 1, there was a need to add a large amount of the cyclic amine, but since in Example 1, the residual amount of the cyclic amine was larger than that in Comparative Example 1, an addition amount of the cyclic amine was small. The carbon dioxide absorbent may be utilized at low cost by adding a cheap acid. A similar tendency was confirmed in combinations of another amine or another acid. In addition, it was confirmed that in the case of increasing the addition ratio of the acid to increase the molar ratio of the acid to the cyclic amine to 2.5, the residual amount of the cyclic amine was decreased.

Note that, in the disclosure, inevitable contamination of impurities is recognized.

Here, some elements are expressed only by element symbols thereof.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A carbon dioxide absorbent, comprising a chain amine, a cyclic amine, and an acid,
wherein a pH of the carbon dioxide absorbent before absorbing carbon dioxide is 9.5-10.8;
the chain amine is a compound of Formula (1):

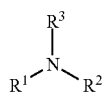

(1)

wherein $R^1$ in Formula 1 is hydrogen or an alkyl chain having at least one hydroxyl group and 1 to 7 carbon atoms,
$R^2$ in Formula (1) is an alkyl chain having at least one hydroxyl group and 1 to 7 carbon atoms, and
$R^3$ in Formula (1) is hydrogen, a straight alkyl chain having 1 to 7 carbon atoms, a branched alkyl chain having 1 to 7 carbon atoms, or a cyclic alkyl chain having 5 to 7 carbon atoms; and
the acid is at least one selected from the group consisting of hydrochloric acid, sulfuric acid, nitric acid, hydroiodic acid, acetic acid, citric acid, formic acid, gluconic acid, lactic acid, oxalic acid, and tartaric acid.

2. The absorbent according to claim 1, wherein a pH of the carbon dioxide absorbent before absorbing carbon dioxide is 9.6-10.7.

3. The absorbent according to claim 1, wherein a molar ratio of the cyclic amine to the acid is 1.0:0.1-1.9.

4. The absorbent according to claim 1, wherein the cyclic amine is at least one compound selected from the group consisting of a compound of Formula (2), a compound of Formula (3), and a compound in which structures of Formulas (2) and (3) are linked with each other by a carbon chain,

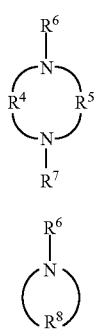

$R^4$ in Formula (2) is an alkyl chain having 1 to 3 carbon atoms, optionally has an organic group including nitrogen as a side chain, and optionally has a hydroxyl group as a side chain, $R^5$ in Formula (2) is an alkyl chain having 2 to 3 carbon atoms, optionally has an organic group including nitrogen as a side chain, and optionally has a hydroxyl group as a side chain, $R^6$ in Formula (2) is hydrogen or a straight or branched alkyl chain having 1 to 4 carbon atoms, and optionally has a hydroxyl group, $R^7$ in Formula (2) is hydrogen or a straight or branched alkyl chain having 1 to 4 carbon atoms, and optionally has a hydroxyl group, $R^8$ in Formula (3) is a straight alkyl chain having 4 to 7 carbon atoms, optionally has an organic group including nitrogen as a side chain, and optionally has a hydroxyl group, and $R^9$ in Formula (3) is hydrogen or a straight or branched alkyl chain having 1 to 4 carbon atoms, and optionally has a hydroxyl group.

5. The absorbent according to claim 1, wherein the acid has pKa of 6.0 or less.

6. The absorbent according to claim 1, wherein the acid is at least one selected from the group consisting of hydrochloric acid, sulfuric acid, nitric acid, and hydroiodic acid.

7. The absorbent according to claim 1, wherein the acid is at least one selected from the group consisting of acetic acid, citric acid, formic acid, gluconic acid, lactic acid, oxalic acid, and tartaric acid.

8. The absorbent according to claim 7, wherein the acid is at least one selected from the group consisting of acetic acid, citric acid, gluconic add, lactic acid, oxalic acid, and tartaric acid.

9. An apparatus of separating and recovering carbon dioxide, the apparatus comprising the carbon dioxide absorbent according to claim 1, the carbon dioxide absorbent being a carbon dioxide unabsorbed carbon dioxide absorbent, the apparatus comprising:
an absorption tower configured to separate and recover carbon dioxide from gas containing carbon dioxide by contacting the gas containing carbon dioxide with the carbon dioxide unabsorbed carbon dioxide absorbent to allow carbon dioxide to be absorbed in the carbon dioxide unabsorbed carbon dioxide absorbent and a carbon dioxide absorbed carbon dioxide absorbent is obtained; and
a regeneration tower configured to regenerate the carbon dioxide absorbed carbon dioxide absorbent by desorbing carbon dioxide from the carbon dioxide absorbed carbon dioxide absorbent which has absorbed carbon dioxide.

* * * * *